(12) United States Patent
Hartgerink et al.

(10) Patent No.: US 9,526,762 B1
(45) Date of Patent: Dec. 27, 2016

(54) MULTIDOMAIN PEPTIDES FOR PROMOTING ANGIOGENESIS

(71) Applicant: WILLIAM MARSH RICE UNIVERSITY, Houston, TX (US)

(72) Inventors: Jeffrey Dale Hartgerink, Pearland, TX (US); Vivek Ashok Kumar, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 14/454,802

(22) Filed: Aug. 8, 2014

Related U.S. Application Data

(60) Provisional application No. 61/863,965, filed on Aug. 9, 2013.

(51) Int. Cl.
| | |
|---|---|
| *A61K 9/127* | (2006.01) |
| *A61K 38/18* | (2006.01) |
| *A61K 47/48* | (2006.01) |
| *A61K 9/00* | (2006.01) |

(52) U.S. Cl.
CPC ......... *A61K 38/1891* (2013.01); *A61K 9/0024* (2013.01); *A61K 47/48246* (2013.01); *A61K 47/48338* (2013.01)

(58) Field of Classification Search
None
See application file for complete search history.

(56) References Cited

U.S. PATENT DOCUMENTS

| | | | |
|---|---|---|---|
| 6,780,836 B2 * | 8/2004 | Unemori | ................. 512/12 |
| 8,022,178 B2 | 9/2011 | Horii et al. | |
| 8,367,639 B2 | 2/2013 | Kiick et al. | |
| 8,415,325 B2 | 4/2013 | Kiick et al. | |
| 8,420,774 B2 | 4/2013 | Murphy et al. | |
| 8,575,311 B2 | 11/2013 | Chmielewski et al. | |
| 8,642,516 B2 | 2/2014 | Koepsel et al. | |
| 8,778,869 B2 | 7/2014 | Murphy et al. | |
| 8,846,860 B2 | 9/2014 | Murphy et al. | |
| 2009/0305994 A1 | 12/2009 | D'Andrea et al. | |
| 2011/0200560 A1 | 8/2011 | Zhang | |
| 2013/0101628 A1 | 4/2013 | Webber et al. | |
| 2014/0235542 A1 | 8/2014 | Levengood et al. | |

OTHER PUBLICATIONS

Dong, et al. "Self-assembly of multidomain peptides: Balancing molecular frustration controls conformation and nanostructure." J. Am. Chem. Soc. 2007; 129(41): 12468-12472.
Aulisa, et al. "Self-assembly of multidomain peptides: sequence variation allows control over cross-linking and viscoelasticity." Biomacromolecules. Sep. 14, 2009; 10(9): 2694-2698.
Galler, et al. "Self-assembling multidomain peptide hydrogels: Designed susceptibility to enzymatic cleavage allows enhanced cell migration and spreading." J. Am. Chem. Soc. 2010, 132: 3217-3223.
Bakota, et al. "Enzymatic cross-linking of a nanofibrous peptide hydrogel." Biomacromolecules 2011, 12: 82-87.
Bakota, et al. "Injectable multidomain peptide nanofiber hydrogel as a delivery agent for stem cell secretome." Biomacromolecules 2011, 12: 1651-1657.
Galler, et al. "Scaffold for Dental Pulp Tissue Engineering." Adv. Dent. Res. 23(3) 2011: 333-339.
Galler, et al. "A customized self-assembling peptide hydrogel for dental pulp tissue engineering." Tissue Engineering: Part A, 2012, 18: 176-184.
Bakota, et al. "Self-assembling multidomain peptide fibers with aromatic cores." Biomacromolecules 2013, 14, 1370-1378.
Wang, et al. "Peptide nanofibers preconditioned with stem cell secretome are renoprotective." J. Am. Soc. Nephrol 2011, 22: 704-717.
Webber, et al. "Supramolecular nanostructures that mimic VEGF as a strategy for ischemic tissue repair." PNAS, vol. 108, No. 33, 13438-13443, Aug. 16, 2011.
Spencer, et al. "Adipose tissue macrophages in insulin-resistant subjects are associated with collagen VI and fibrosis and demonstrate alternative activation." Am. J. Physiol Endocinol. Metab 2010, 299: E1016-E1027.
Maess, et al. "Selection of reliable reference genes during THP-1 monocyte differentiation into macrophages." BMC Molecular Biology 2010, 11:90.
Lin, et al. "Regulating MCP-1 diffusion in affinity hydrogels for enhancing immuno-isolation." J. Control Release 2010, 142(3): 384-391.

\* cited by examiner

*Primary Examiner* — Karlheinz R Skowronek
*Assistant Examiner* — Sergio Coffa
(74) *Attorney, Agent, or Firm* — Reed Smith LLP; Robert R. Riddle; Matthew S. Gibson

(57) ABSTRACT

The present disclosure provides a composition comprising a multi-domain peptide capable of self-assembly into a nanofibrous hydrogel structure capable of stimulating a robust angiogenic response. In one embodiment, the composition comprises a short 15 amino acid VEGF-165 peptide mimic conjugated to a 16 amino acid multidomain peptide. A method for promoting angiogenesis and/or treating ischemic wounds in a subject is also provided.

18 Claims, 17 Drawing Sheets
(6 of 17 Drawing Sheet(s) Filed in Color)

FIGS. 1B-D
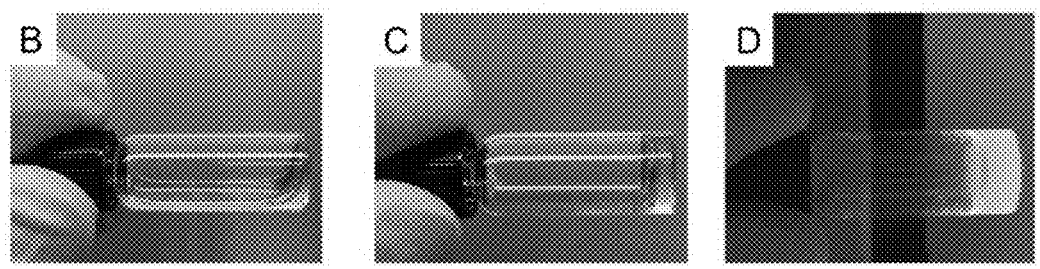
FIGS. 1E-G
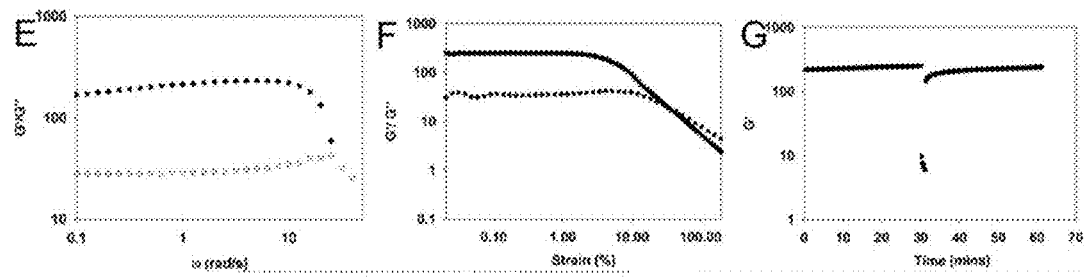

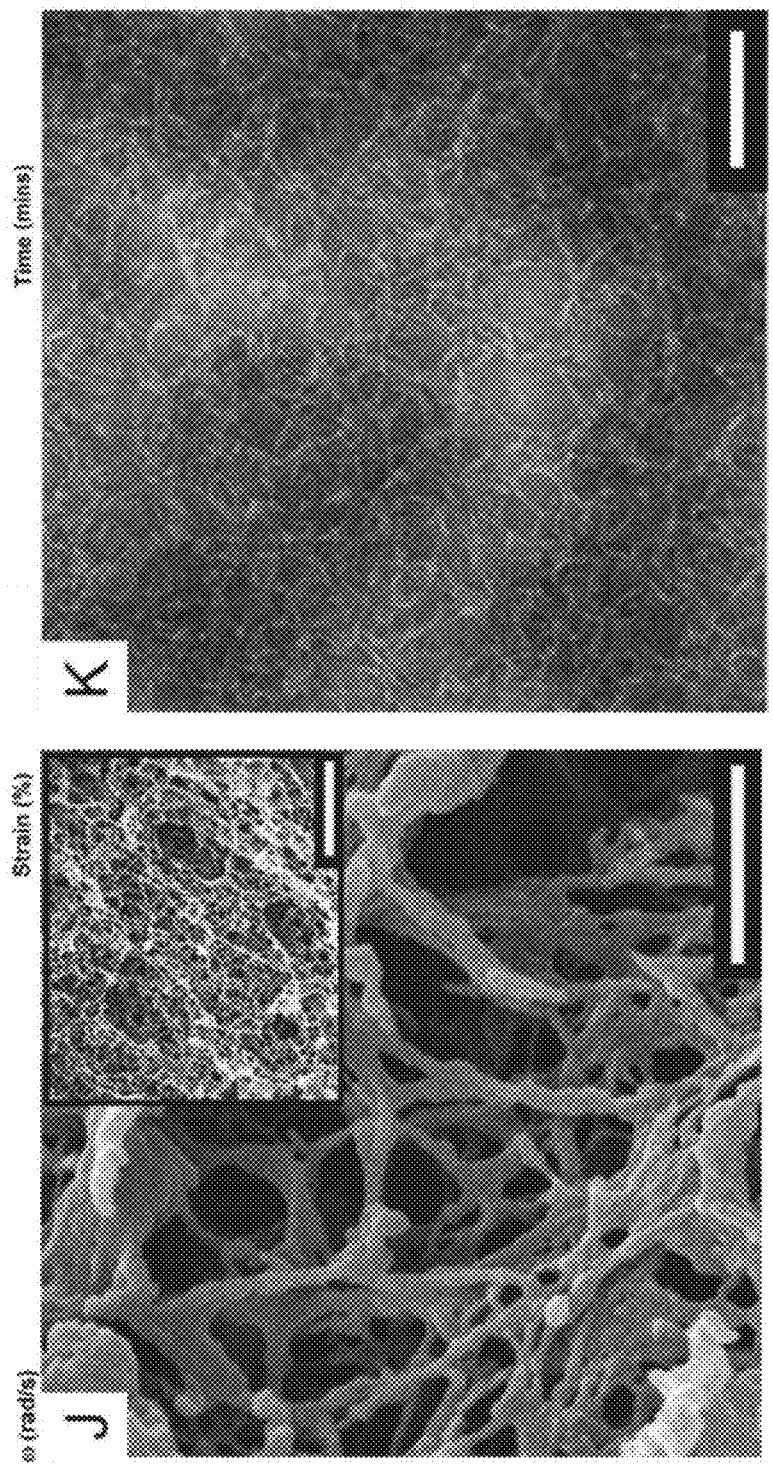

FIGS. 3B-F
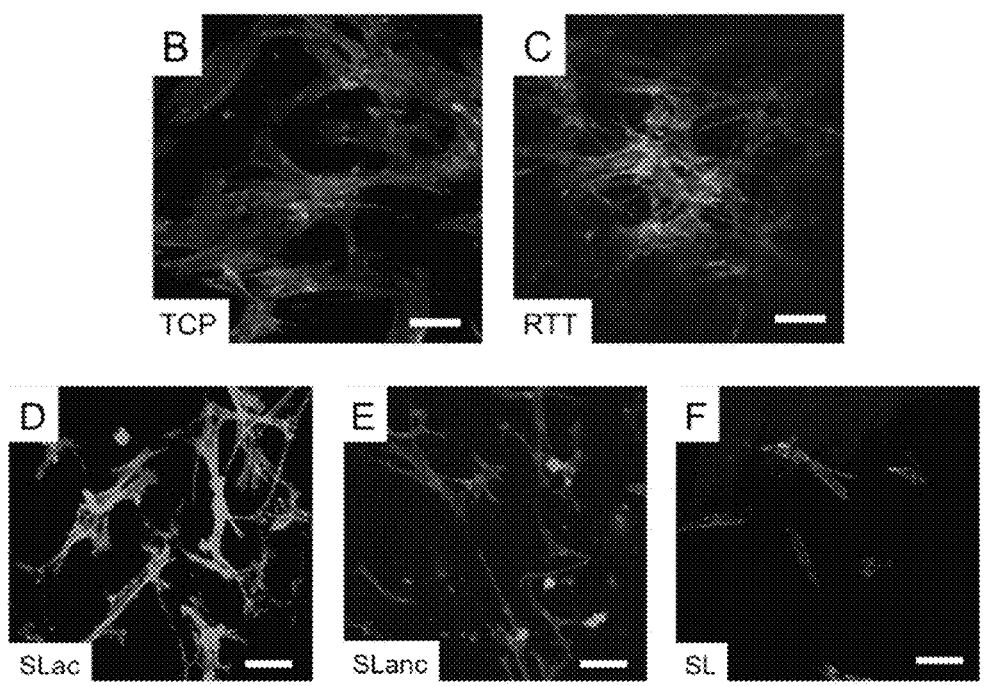

FIGS. 3G-H
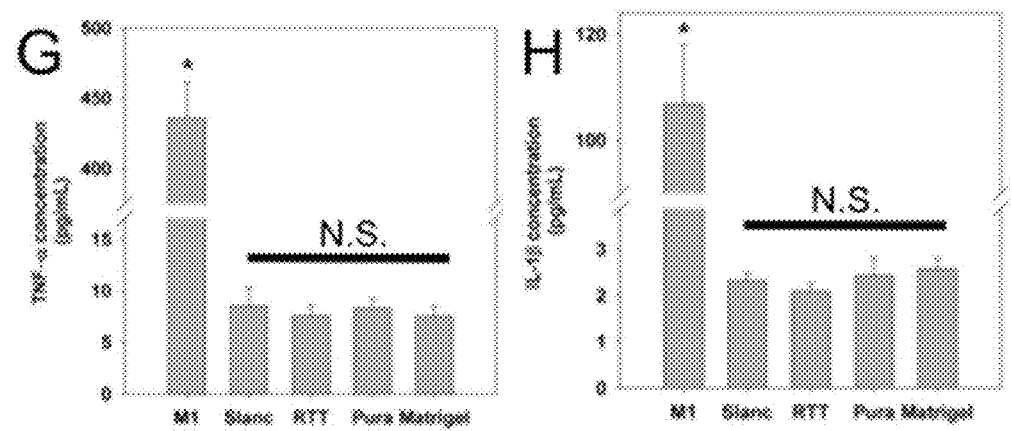

FIGS. 3K-L
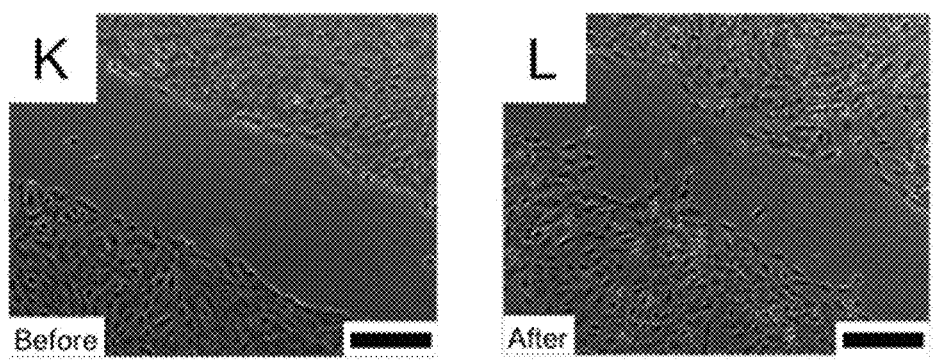

FIGS. 4B-C
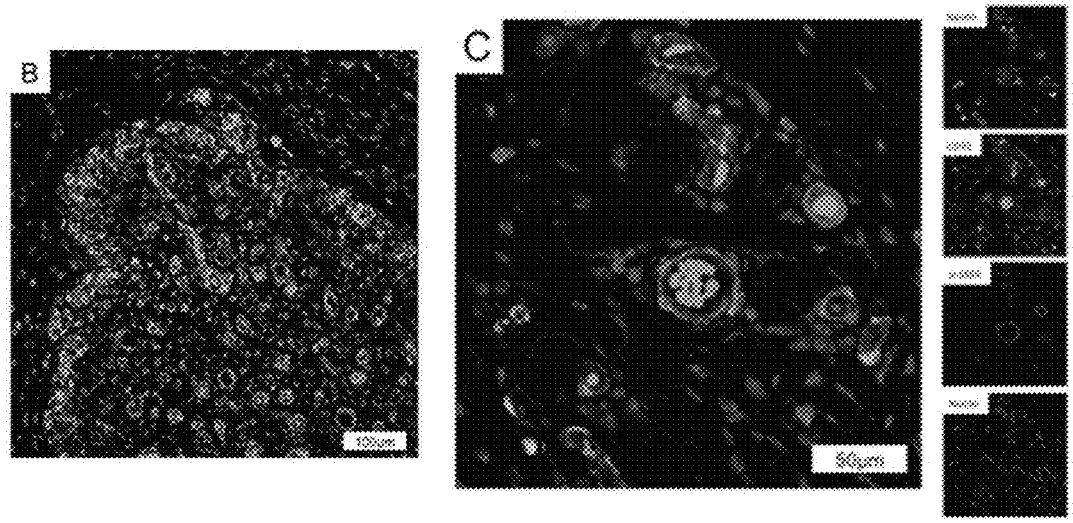

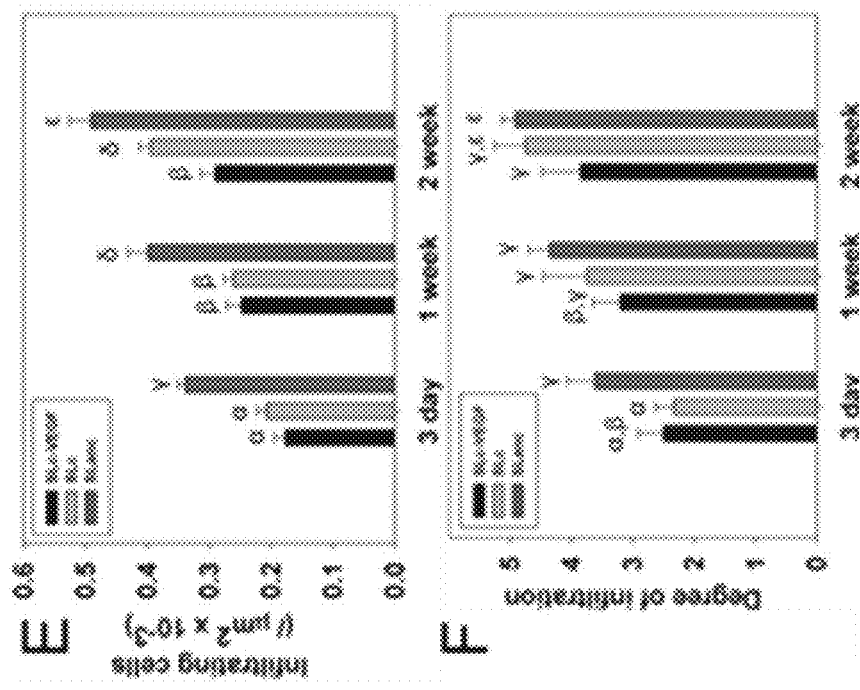
FIGS. 4E-F

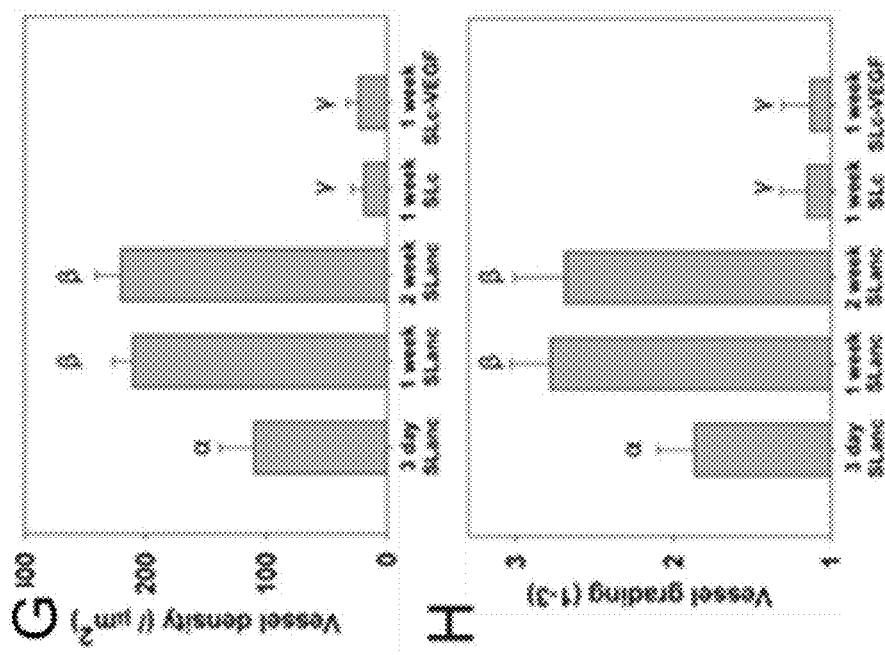
FIGS. 4G-H

MULTIDOMAIN PEPTIDES FOR PROMOTING ANGIOGENESIS

MULTIDOMAIN PEPTIDES FOR PROMOTING ANGIOGENESIS

CROSS REFERENCE TO RELATED APPLICATIONS

The present application claims priority to U.S. Provisional Application No. 61/863,965 filed Aug. 9, 2013, which is incorporated herein by reference in its entirety.

STATEMENT OF GOVERNMENT INTEREST

This invention was made with government support under Grant Numbers R01 DE021798 and F32 DE023696 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 6, 2014, is named 13-21114-us_SL.txt and is 21,786 bytes in size.

BACKGROUND

Neovascularization of ischemic wounds, limb, myocardium, dental pulp and neural tissue is a vital treatment modality to prevent hypoxia, apoptosis and tissue necrosis while augmenting tissue regeneration. Current techniques to achieve blood vessel growth (angiogenesis) have focused on: i) modulating inflammation using cytokines (eg. IL-4, IL-10, MCP-1) to promote a proangiogenic M2 macrophage phenotype; ii) injecting a host of growth factors (eg. P1GF, FGF, EGF, VEGF); iii) mesenchymal stem cell transplantation; and iv) gene therapy for the induction of VEGF production. These therapies to achieve neovascularization have been hampered by low gene uptake, neoplasticity, immune rejection and maladaptive inflammatory responses. Clinical trials have been met with modest success and have failed to fully functionally recover ischemic tissue. Treatment with vascular endothelial growth factor (VEGF) has resulted in modest reversal of ischemia with much of the non-sequestered growth factor diffusing into the lymphatic system.

Promotion of angiogenesis can be stimulated by a host of factors as detailed above. However, current techniques result in small nascent vessels that either fail to anastomose with host vasculature, are immature lacking supporting pericytes, or resorb too quickly over a less than 1 week period. In coming to the present invention, three vital criteria were identified for the development of a proangiogenic material: 1) retention of vessels for long 1-2 week periods; 2) development of mature stable vessels that have a pericyte/muscular wall; and 3) efficient resorption after functional recovery. To date, the therapeutic approaches described above have failed to demonstrate success on all three criteria.

SUMMARY

A composition for promoting angiogenesis and for use in other therapeutic applications is provided. In one embodiment, the composition comprises a peptide with five domains. A first domain comprises one to four repeats of a negatively or positively charged amino acid. In this embodiment, the first domain is located at both the N-terminus an C-terminus of a second domain. The second domain comprises two to six repeats of an amino acid sequence consisting of a hydrophilic amino acid and a hydrophobic amino acid. The second domain drives the self-assembly of the peptide into a β-sheet structure. A third domain comprises a specific enzymatic cleavage signaling sequence. The third domain, in at least one embodiment, is embedded within the second domain. A fourth domain provides a spacer between, in at least one embodiment, the first domain and the fifth domain. The fifth domain comprises a bioactive peptide sequence. This sequence is active both within the peptide or when cleaved from the parent peptide. Upon adding the peptide to a charged buffer, the peptide self-assembles to form a hydrogel scaffold. The hydrogel structure quickly recovers following disruption through shearing thereby allowing the composition to be injected non-invasively or minimally invasively with a syringe-needle or catheter delivery. Thus, more invasive implantation procedures can be avoided. Moreover, the addition of a cleavage signal in the peptide facilitates diffusion of the bioactive peptide enhancing its biological effect as well as promoting biodegradation of the composition.

A method is also provided. In one embodiment, the method comprises administering a composition of the present disclosure to a target location of a subject and allowing the composition to form a hydrogel scaffold at the target location following administration. Due to the properties of the present composition, the step of administering the composition can be performed non-invasively via injection. In certain embodiments, the subject is a human patient that has suffered an ischemic wound and the composition administered provides a peptide that promotes angiogenesis at the site of the wound.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1B-D depict a viscous solution (B) where SLanc self-assembled into beta sheets due to hydrophobic interactions and (C) depicts a solution where the terminal lysine of SLanc is stabilized by multivalent anions such as phosphate buffer. (D) FITC modified SLanc (F-Slanc) was added to SLanc (1:100) and gelled—yielding fluorescent hydrogels.

FIGS. 1E-G provide graphs demonstrating the rheometry of 1 w % SLanc gels in sucrose-HBSS showed gels starting to break down at 30 rad/s (E), 30% strain (F), and recovery from high shear (G).

FIG. 1J provides a scanning electron microscopy image of SLanc (scale bar 1 μm, inset 10 μm) demonstrating a fibrous matrix structure.

FIG. 1K provides a transmission electron microscopy image of SLanc (scale bar 100 nm) demonstrating a fibrous matrix structure.

FIGS. 3B-F provide representative images of hMSC adhered and spread on the following scaffolds: (B) TCP, (C) RTT, (D) SLac, (E) SLanc and (F) SL, scale bar 100 μm.

FIGS. 3G-H provide graphical representations of inflammatory potential of various scaffolds measured by incubating THP-1 cells atop the various scaffolds and measuring TNF-α (G) and IL-1β (H) secretion.

FIGS. 3K-L provide representative images of a SLanc healed scratch wound (K) before, (L) after exposure to SLanc, scale bar 250 μm. Similar Greek letter indicates no statistically significant difference (*p<0.01).

FIGS. 4B-C depict immunostaining of cells from hematopoietic and mesenchymal origin showing extensive infiltration of pericyte-like cells (purple—Nestin+), which co-stain with SMC (red—α-SMA+), surrounding endothelial cells in large stable microvessels and circulating cells (green—CD31+); (C) provides a selected magnified region of (B).

FIGS. 4E-F provide a graphical representation of the quantification of infiltrating cells showing significantly greater cellular population of SLanc scaffolds, p<0.01(E), towards the center of scaffolds (F).

FIGS. 4G-H provide a graphical representation of the quantification of tube formation (G) and vessel maturity (H) demonstrating the efficacy of SLanc in promoting angiogenesis, venulo-/arteriolo-genesis.

DETAILED DESCRIPTION

Figure 1A:
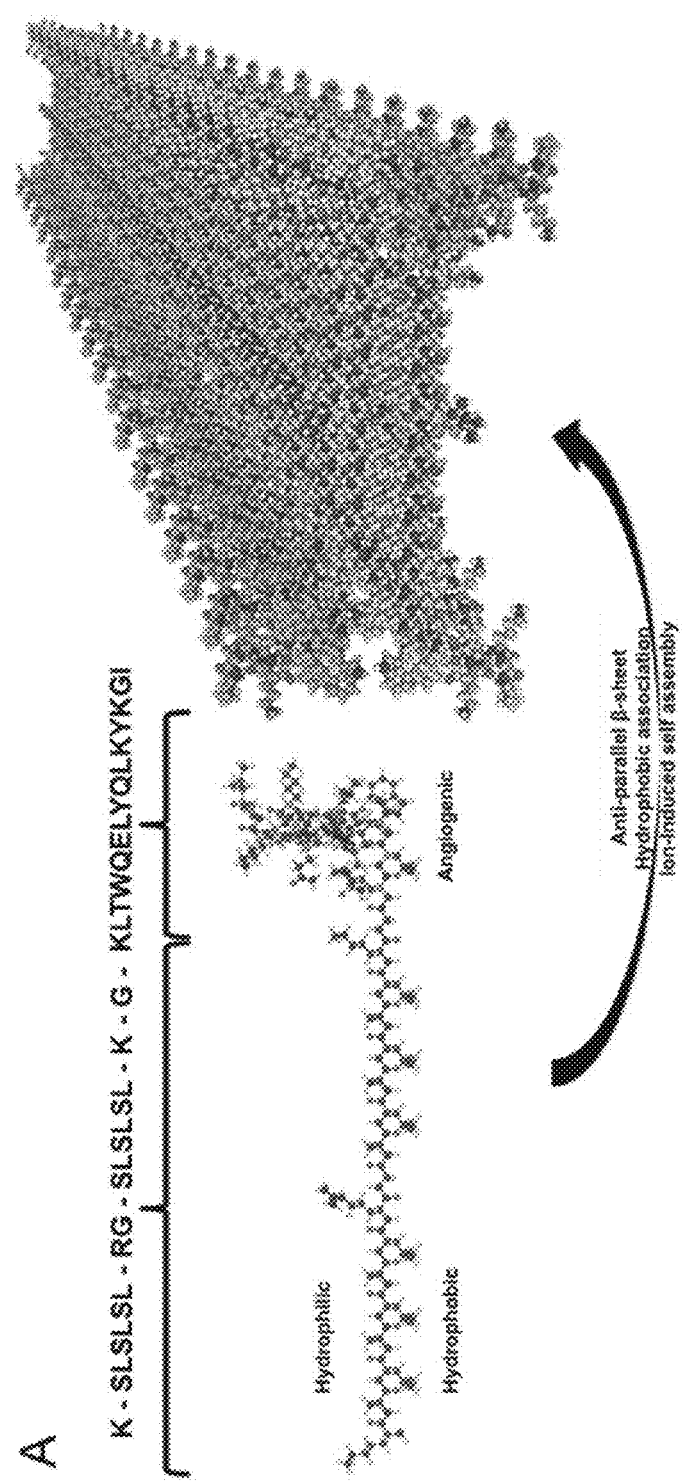
FIG. 1A depicts the structure of one embodiment of a multidomain peptide (MDP) comprising an MMP-2 cleavage site (-RG-), terminal lysine residues, alternating facially separating hydrophilic and hydrophobic residues, and a glycine spacer and a VEGF-165 mimic (peptide referred to herein as "SLanc").

The present disclosure is directed to compositions and methods comprising multidomain peptides (MDPs) that self-assemble into extracellular matrix (ECM) mimetic nanofibrous hydrogels. Generally, MDPs comprise terminally charged residues (first domain) that flank alternating hydrophobic and hydrophilic residues (second domain). These facial amphiphiles associate into anti-parallel β-sheets excluding polar solvents. Self-assembling peptides form short-range fibrils due to molecular frustration between like-like terminal charges. With the addition of multivalent ions (such as a PBS), charges on terminal residues are shielded, allowing long-range fiber growth, entanglement and hydrogel formation from millimolar concentration solutions. Van der Waal's and hydrophobic interactions promote peptide self-assembly. These bonds easily break and reform to allow shear thinning and near instantaneous (within 60 to 90 seconds) recovery (90-95% G' of initial storage modulus of the peptide structure) allowing for aspiration and needle in situ delivery of the nanofibrous hydrogels.

The peptides of the present compositions comprise a first domain that includes positively or negatively-charged residues that flank the alternating hydrophobic and hydrophilic residues of a second domain. In one embodiment, the terminally charged residues of the first domain include, for example, one to four repeats (i.e. 1-4 amino acids on each end of the second domain) of glutamic acid, aspartic acid, arginine, histidine, or lysine. In one particular example, a single lysine residue is positioned at both the N-terminal and C-terminal ends of the second domain.

The peptides of the present compositions comprise a second domain that promotes self-assembly of the peptide to a hydrogel structure when present in buffers of appropriately charged ions. In one embodiment, the second domain includes alternating hydrophobic and hydrophilic amino acid residues. Non-limiting examples of suitable hydrophobic amino acid residues includes alanine, leucine, glycine, isoleucine, tryptophan, phenylalanine, proline, methionine, and cysteine. Non-limiting examples of suitable hydrophilic amino acid residues includes serine, tyrosine, threonine, asparagine, and glutamine. The second domain may include two to eight repeats (i.e., 4-16 amino acids) of the hydrophobic/hydrophilic or hydrophilic/hydrophobic sequence. In one embodiment, the second domain comprises six repeats of serine-leucine (12 amino acids).

The third domain of the peptide of the present compositions is an enzymatic cleavage signaling sequence. The enzymatic cleavage signaling sequence of the present disclosure is directed to a sequence that actually signals and results in a specific cleavage event to at least a portion of the peptide content of the composition. For example, the enzymatic cleavage signaling sequence includes sequences specifically recognized by enzymes secreted by tissues or cells, such as macrophages or fibroblasts, invading or surrounding the administration site of the composition. In one embodiment, the enzymatic cleavage signaling sequence is recognized and cleaved by a matrix metalloprotease (MMP) such as those described in Table 1 of Turk, et. al., *Nature Biotechnology*, 661-667 (2001). In one embodiment, the enzymatic cleavage signaling sequence is susceptible to cleavage by MMP-2 and is leucine-arginine-glycine. The enzymatic cleavage signaling sequence may be separate from the other domains of the peptide or may be embedded in another domain. For example, the cleavage sequence may be placed within the second domain and more specifically, in the middle of the second domain. In the instance the second domain comprises a sequence of six repeats of serine-leucine, the cleavage sequence can be positioned after the third repeat such. For example, the first, second, and third domains may comprises a sequence of KSLSLSLRG- SLSLSLK (SEQ ID NO: 1). In this example, the leucine of the cleave sequence—LRG—is provided by the third repeat of the second domain. In other embodiments, the enzymatic cleavage sequence may be between the second domain and fourth domain, within the fourth domain, between the first and second domain (on the C-terminal end), between the fourth domain and fifth domain, and within the fifth domain to the extent the cleaved portion of the bioactive peptide sequence remains active.

The peptides of the present compositions further include a fourth domain comprising a spacer. As used herein, the term "spacer" denotes one or more amino acids or a different molecular entity that are generally small and nonpolar in order to minimize the likelihood of interference with self-assembly of the peptide. An amino acid spacer group may include, for example, aminohexanoic acid, polyethyleneglycol, 5 or less repeats of glycine, and 3 or less repeats of glycine-glycine-serine-glycine (SEQ ID NO: 95).

The fifth domain of the present peptide compositions comprises a bioactive peptide sequence. As used herein, a "bioactive peptide sequence" is an amino acid sequence of a peptide that induces a phenotypic response or molecular or cellular change in an appropriate cell type or tissue when the cell or tissue is contacted with the peptide. In some instances, the bioactive peptide sequence represents an active or response-inducing portion of a larger polypeptide. Non-limiting examples of bioactive peptide sequences suitable for use in the present compositions and methods is provided in Table 1.

TABLE 1

Examples of Bioactive Peptide Sequences

| Epitope | Sequence | SEQ ID NO: |
|---|---|---|
| rh-BMP-2 | YPVHPST | 2 |
| rh-TGF-.beta.1 | LPLGNSH | 3 |
| BMP-2 and TGF-.beta.1 | LHYPFMT | 4 |
| | LPLGNSH | 5 |
| | RTTSPTA | 6 |
| | KVPPANT | 7 |
| | QQTQAQH | 8 |
| | LRNYSHS | 9 |
| | GKYPPTS | 10 |
| | KQALTQT | 11 |
| | PIQPDER | 12 |
| | VYRHLPT | 13 |
| | AWKSVTA | 14 |
| | WPALFTH | 15 |
| | PFDPPVR | 16 |
| | RVSTWDT | 17 |
| | LPSPIQK | 18 |
| | PGPTVQG | 19 |
| | DVSPAYH | 20 |
| | PAPRWIH | 21 |
| BMP-2 | V.sub.6K.sub.3SG.sub.3YPVHPST | 22 |
| TGF-.beta.1 | V.sub.3A.sub.3K.sub.3SG.sub.3LPLGNSH | 23 |
| VEGF | WPTWVNN | 24 |
| | PTPLKVRLHSYN | 25 |
| | YYTVHHM | 26 |
| | WHWSLNH | 27 |
| | VSILSTIPNSMT | 28 |
| | SWWAPFH | 29 |
| | FTEPLAS | 30 |
| | PLTPSALLPIFE | 31 |
| | THAFRVM | 32 |
| | ASLFSSN | 33 |
| | LPQKNTIQYEKM LLTVSSY | 34 |
| | LPYPHYH | 35 |
| | KLTWQELYQLKYKGI | 36 |

TABLE 1-continued

Examples of Bioactive Peptide Sequences

| Epitope | Sequence | SEQ ID NO: |
|---|---|---|
| FGF-2 | PMHHHKH | 37 |
| | AQVRSGD | 38 |
| | KHPPTNW | 39 |
| | AMLSHLS | 40 |
| | DFIQPYQ | 41 |
| | VYWSRIE | 42 |
| | AMPQRPL | 43 |
| | HSRHFHH | 44 |
| | RMTQVPL | 45 |
| | LSTPPLR | 46 |
| NT-3 | HTTEILH | 47 |
| | PSNYQTS | 48 |
| | SYFPSSA | 49 |
| | EARQSYS | 50 |
| | DEPQKAH | 51 |
| | TLGLGLH | 52 |
| | YMRRSLS | 53 |
| | VVLYLPL | 54 |
| Laminin-5 | SKLNTKS | 55 |
| | PTYHHRH | 56 |
| | LRHKSLH | 57 |
| | RYHPHLH | 58 |
| | GRYHHYLH | 59 |
| BMP-2 | KIPKASSVPTEL | 60 |
| heparin proteoglycan | KRTGQYKL | 61 |
| fibronectin-derived cell adhesion peptide | GRGDSP | 62 |
| Fibronectin/endothelial cells adhesion | GRGESP | 63 |
| Osteopontin | SVVYGLR | 64 |
| Actin binding site on thymosin β4 | LKKTETQ | 65 |
| Elastin/endothelial cell migration and tubulogenesis | VGVAPG | 66 |
| | REDV | 67 |
| Repetitive RGD Others | PRGDSGYRGDS | 68 |
| | RGD | |
| | GGGKLTWQELYQLKYKGI | 69 |
| | SDPGYIGSR | 70 |
| | GRNIAEIIKDI | 71 |
| | DITYVRLKF | 72 |
| | DITVTLNRL | 73 |
| | GRYVVLPR | 74 |
| | GNRWHSIYITRFG | 75 |
| | SIDQVEPYSSTAQ | 76 |
| | KIPKASSVPTELSAISTLYL | 77 |
| | KKQRFRHRNRKG | 78 |
| | GASIKVAVSADR | 79 |
| | GTTVKYIFR | 80 |
| | GSIKIRGTYS | 81 |
| | GSINNNR | 82 |

In one embodiment, a sequence accounting for a portion of VEGF constitutes the bioactive peptide sequence. For example, the bioactive sequence may be KLTWQELYQLKYKGI (SEQ ID NO: 36). Thus, in certain embodiments, the peptide of the present compositions and methods is K-SLSLS-LRG-SLSLSL-K-G-KLTWQELYQLKYKGI (SEQ ID NO: 83). As demonstrated in the below Examples, this peptide, also referred to herein as "SLanc," may be used to promote angiogenesis and neovascularization at, for example, an ischemic wound site of a subject.

The peptides of the present composition such as SLanc can be lyophilized and dissolved in, for example, an appropriate concentration of sucrose solution or in deionized water. In one embodiment, the peptides can be provided in a 1-300 mM sucrose solution. The peptide concentration in the solution may be from about 0.1 mg/ml to about 100 mg/ml, from about 1 mg/ml to about 90 mg/ml, from about 10 mg/ml to about 80 mg/ml, from about 20 mg/ml to about 70 mg/ml, from about 30 mg/ml to about 60 mg/ml, from about 40 mg/ml to about 50 mg/ml, and any concentration therebetween.

The compositions of the present disclosure may, in some embodiments, further comprise a buffer comprising positively or negatively-charged ions. In the instance the first domain is a positively charged amino acid, such as lysine, the buffer comprises negatively-charged ions, such as a buffered solution containing multivalent salts such as $PO_4^{3-}$. Conversely, where the first domain is a negatively-charged amino acid, an appropriate buffer comprises positively-charged ions, such as phosphate buffered solution, Hanks balanced salt solution which contain positively charged monovalent and multivalent ions such as $Na^+$, $Mg^{2+}$, $Ca^{2+}$ or heavy metals that can facilitate in vivo imaging such as gadolinium ions. In the presence of such appropriate buffers, peptides of the present composition self-assembles into β-sheets thereby forming a nanofibrous hydrogel scaffold. The peptides may be added to the buffer to provide a final peptide concentration of from about 0.05 mg/ml to about 50 mg/ml, from about 1 mg/ml to about 40 mg/ml, from about 2.5 mg/ml to about 30 mg/ml, from about 5 mg/ml to about 25 mg/ml, from about 10 mg/ml to about 20 mg/ml, and any final concentrations therebetween. Further, given the nature of self-assembly utilizing hydrophobic and hydrophilic interactions and ionic interactions, these bonds easily break and reform on the molecular level thereby demonstrate near instantaneous (less than or about 90 seconds following shear exposure) shear recovery (>90-95% G') after intermittent high shear events (e.g. 1 minute shear exposure at 100% strain) such as needle aspiration or needle delivery, even at final peptide concentrations greater than 5 mg/ml. As such the hydrogel compositions are injectable at high peptide concentrations. This provides a distinct advantage over other hydrogel scaffold systems that do not possess shear recovery and must therefore be implanted as a formed hydrogel and as well from other injectable hydrogel systems that only recover at lower concentrations, such as less than 5 mg/ml.

The present disclosure also provides methods of treating various diseases or conditions using the compounds described herein. In one embodiment, the method comprises administering any one of the above described composition to a target location of a subject; and following administration, allowing the composition to form a hydrogel scaffold at the target location. For example, where the peptide is SLanc or includes another angiogenesis-promoting peptide sequence, the method comprises administering the composition to a human or animal subject that has suffered an ischemic wound such that the composition is administered directly to the site of the ischemic wound to promote neovascularization and angiogenesis thereby enhancing healing. Due to the shear recovery properties of the present compositions, the administering step can be performed through injection with a syringe and needle or some other non-invasive technique that results in sheer thinning of the peptide. Furthermore, the composition can be injected at high final peptide concentrations such as greater than 5 mg/ml to about 50 mg/ml, from about 10 mg/ml to about 20 mg/ml, and all concentrations therebetween. This allows for the subject to receive a higher bioactive peptide concentration which enhances the desired therapeutic effect. Furthermore, given the injectability, cytocompatibility, biocompatibility, biodegradability, and in vivo angiogenesis, multiple injections can be performed directly into ischemic tissue, proximal and/or distal to ischemic lesions, and performed multiple times over periods of seconds, minutes, hours, weeks, months or longer.

Unless otherwise indicated, all numbers expressing quantities of ingredients, concentrations properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any instance, embodiment, or example discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

EXAMPLES

To facilitate a better understanding of the present invention, the following examples of specific instances are given. In no way should the following examples be read to limit or define the entire scope of the invention.

The following materials and methods were employed for the Examples below.

Peptide Design and Characterization

Multidomain peptides were designed as follows: base peptide SL: $K_2$-$(SL)_6$-$K_2$ (SEQ ID NO: 84); cleavage peptide SLc: $K_2$-$(SL)_3$(RG)$(SL)_3$-$K_2$ (SEQ ID NO: 85); and adhesion and cleavage peptide SLac: K-$(SL)_3$-(RG)-$(SL)_3$-K-(GRGDS) (SEQ ID NO: 86): angiogenic peptide SLanc: K-$(SL)_3$(RG)$(SL)_3$-K-G-KLTWQELYQLKYKGI (SEQ ID NO: 83). All peptides, resin and coupling reagents were purchased from Aapptec (Louisville, Ky.). Standard solid phase peptide synthesis was performed, Apex Focus XC (Aapptec), using Rink amide resin with 0.37 mM loading and N-terminal acetylation. Post cleavage from resin, crude mass was checked prior to dialysis with 500-1200 MWCO dialysis tubing (Sigma-Aldrich, St. Louis, Mo.) against DI water. Peptides were subsequently lyophilized, confirmed for purity using electron-spray ionization mass spectrometry, MicroTOF ESI (Bruker Instruments, Billerica, Mass.), and reconstituted at 20 mg/mL in sterile 298 mM sucrose. Gelation of peptide was achieved by addition of volume equivalents of pH 7.4 buffer with 1× divalent negatively charged salts (PBS/HBSS). For certain studies comparison to biosynthetic scaffolds was performed. Scaffolds used include: acid solubilized Type I rat tail tendon collagen (RTT) (4.0 mg/mL neutralized), Matrigel™ (8.2 mg/mL), Puramatrix™ (PURA) and tissue culture polystyrene (TCP) were all obtained from BD Biosciences (Franklin Lakes, N.J.).

Scanning Electron Microscopy (SEM) and Transmission Electron Microscopy (TEM)

Microscopic morphology of SLanc scaffolds was determined using SEM and TEM. For SEM, samples were ethanol dehydrated, critical point dried, sputter coated with 7 nm gold (Denton, Moorestown, N.J.), and imaged using a FEI Quanta 400 ESEM (FEI Company, Hillsboro, Oreg.). Fibrillar network for SLanc was confirmed using TEM. For TEM, samples were prepared by adding peptide solution directly onto Quantifoil R1.2/1.3 holey carbon mesh on copper grids. Excess peptide was blotted and the grid was dried prior to negative staining using 2.0% pH 6 phototungstic acid for 10 min. Dried grids were imaged using a JEOL 2010 microscope (200 kV).

Circular Dichroism

All circular dichroism experiments were performed on a Jasco J-815 spectropolarimeter equipped with a Peltier temperature controller. All spectra were collected from 185-250 nm at 37° C. Samples were prepared at pH 7.4 by diluting peptide in either ultrapure Milli-Q water or Hank's Balanced Salt Solution (HBSS) at 1 wt %. Samples were then allowed to incubate at room temperature for 4 days before spectra was run. For each experiment, 100 µL aliquots of each sample were transferred to a Quartz cell with a path length of 0.01 mm. The molar residual elipticity (MRE) was calculated from the following formula:

$$[\hat{I}_i] = \frac{\hat{I}_i * m}{C * n_r * l}$$

where θ is the observed ellipticity in millidegrees, m is the molecular weight in g-mol−1, C is the concentration in mg-ml−1, l is the path length of the cuvette in cm, and nr is the number of amino acids in the peptide.

Attenuated Total Reflectance Infrared Spectroscopy (ATR-IR)

Peptide gel at pH 7.4 was pipetted onto a "Golden Gate" diamond window and dried under nitrogen until a thin film of peptide was achieved. IR spectra (32 accumulations) were taken using a Jasco FT/IR-660 spectrometer.

Mechanical Analysis

Peptide solutions were made by dissolving lyophilized SLanc in 298 mM sucrose-water at a concentration of 2 w %, pH 7.4. Hydrogels were constructed by addition of Hank's balanced salt solution (HBSS) at a 1:1 ratio. Thus final peptide concentration in hydrogels was 1% wt. Negatively charged polyvalent ions in buffer solution formed intermolecular ion interactions with lysine residues, crosslinking the hydrogel. Rheological behavior of peptide hydrogels was determined using an 8 mm parallel plate geometry at a gap of 250 µm. 50 µL of hydrogel was constructed and, within 30 min, placed on stainless steel platens of a rheometer (AR-G2, TA Instruments). A frequency sweep (0.1-100 Hz, at constant 1% strain), strain sweep (0-1000% strain, at 1 Hz) and shear recovery (1% strain for 30 min, 100% strain for 60 s, 1% strain for 30 min) were performed. A phase angle δ<90° was used to ensure no slipping.

Cytocompatibility with Human Mesenchymal Stem Cells and Human Umbilical Vein Endothelial Cells SLanc, SLac, SL, and RTT hydrogels (50 µL) were cast in 16-well chamber slides (n=6). hMSC (2000 on each gel) were seeded, and compared to TCP surfaces. Cells were incubated for 5 days at 37° C. Actin filaments were stained with Alexafluor Phalloidin 488 (Life Technologies) and DAPI (Life Technologies). Cell morphology was noted and nuclei counted to quantify proliferation.

Scratch Wound Healing Assay

HUVEC were seeded in a 12-well plate (25,000 per well) and grown to confluence (n=6). A scratch wound was made in each of the wells with a 1 mL pipet tip. Cell surfaces were then washed with HBSS. Cell culture media with 0.5% FBS and 1 µM peptides (SLanc, SLac, PBS) alone was added on top of cells, n=6. Surfaces were imaged immediately. Cells were then incubated at 37° C. for 18 h imaged again in the same location. NIH Image J was used to measure the infiltration distance by migrating HUVEC.

VEGF Mimetic Sequence Specific Interactions

HUVECs were plated at 2×105 cells per 100 mm petri dish and cultured in full media overnight. Cells were then starved for 24 hr in quiescent media (QM)—Medium 200 with 0.1% FBS. Peptides (SL, SLac, SLanc) were dissolved in QM (50 nM) and added to cells. VEGF was used as a positive control (25 ng/mL) for 24 hr, and TCP with no treatment was used as a negative control. PCR was used to characterize HUVEC phenotypic expression, n=5 for 3 independent repeats. RNA extraction was performed as per manufacturer's protocol (RNeasy, Qiagen, Gaithersburg, Md.). RNA concentrations was determined using Nanodrop (Thermo Scientific, Waltham, Mass.), and reverse transcription to cDNA was performed using iScript (Qiagen), followed by RT-PCR using a Biorad 7300 (Biorad, Berkeley, Calif.) and SsoAdvanced SYBR-green KIT (Qiagen). PCR primers were purchased from Invitrogen. Primers: Vascular endothelial growth factor receptor 1—VEGFR-1 forward: 5-TCCCTTATGATGCCAGCAAGT-3 (SEQ ID NO: 87); VEGFR-1 reverse: 5-CCAAAAGCCCCTCTTCCAA-3 (SEQ ID NO: 88); Vascular endothelial growth factor receptor 2—VEGFR-2 forward: 5-CACCACTCAAACGCT-GACATGTA-3 (SEQ ID NO: 89), VEGFR-2 reverse: 5-GCTCGTTGGCGCACTCTT-3 (SEQ ID NO: 90); Neuropilin 1—NP-1 forward: 5-ATCACGTGCAGCT-CAAGTGG-3 (SEQ ID NO: 91), NP-1 reverse: 5-TCAT-GCAGTGGGCAGAGTTC-3 (SEQ ID NO: 92); Housekeeping ribosomal 60s subunit L37-a forward primer: ATTGAAATCAGCCAGCACGC (SEQ ID NO: 93), L37a reverse primer: AGGAACCACAGTGCCAGATCC (SEQ ID NO: 94), CT values were generated by the software were compared to L37-a expression. Expression of gene of interest was normalized to control expression noted in each experiment.

Immunogenicity with THP-1 Cells

200 µL gels were cast in 24 well plates. Rat tail tendon (RTT), Puramatrix™ (Pura) and Matrigel™ were used as gel controls, and TCP with macrophages differentiated to M1 (20 ng/mL IFN-γ+LPS) and M2 (20 ng/mL IL-4) phenotype were used as cell controls. THP-1 cells in suspension were suspended in media and incubated at a concentration of 1M cells/well atop scaffolds. Media aliquots were assayed for inflammatory (IL-1β, TNF-α), and anti-inflammatory (IL-10) at 24 hr using ELISA (Biolegend, Calif.).

Subcutaneous Implants in Rats

Female Wisar rats (225-250 g, Charles River Labs, Wilmington, Mass.) were anesthetized using isofluorane (2% for induction and 1% for maintenance), dorsal aspect shaved and sterilely prepped. Hydrogel scaffolds of each SL, SLc, SLac, SLanc or controls: Pura, VEGF (1 μg/mL) were made were loaded in syringes with 22 gage needles. 200 μL subcutaneous injections were injected in 4 different 1.5 inch spaced randomized sites on the dorsal aspect, on either side between the lower thoracic and upper lumber vertebrae. At prescribed timepoints 3 day, 1 week, 2 weeks and 1 month rats were euthanized using an overdose of isoflurane, CO2 asphyxiation, and bilateral thoracic puncture. The dorsal skin was removed around the entire implant, washed with PBS, and fixed in neutral buffered formalin for 24 hr prior to processing.

Histologic and Angiogenic Evaluation

Tissue was processed to paraffin blocks, sectioned at 7 μm, deparraffinized and stained for cellular infiltrate using H&E. Cellular infiltrate was determined using immunostaining Mural cell staining associated with angiogenesis was determined by staining for endothelial cells: goat anti-rat CD31+ (Santa Cruz Biotechnology), mouse anti-rat vWF (ABCam); smooth muscle cells: rabbit anti-rat α-SMA+ (Dako); pericytes: mouse anti-rat Nestin+ (Millipore); hematopoitic stem cells: mouse anti-rat CD45 (Santa Cruz Biotechnology), and nucleic DAPI counterstain. Secondary antibodies used were goat anti-rabbit AF 488, donkey anti-goat AF 488, anti-goat AF 488 (Life Technologies), donkey Streptavidin AF 647 (Life Technologies), goat anti-mouse AF 647 and donkey anti-rabbit AF 647. Angiogenesis was quantified by measuring the diameter of vessels (small axis for non-circular vessels), density of vessels (vessels per unit area), presence and thickness of vessel wall (graded from 1 to 3: 1—non-contiguous vessel wall, 2: contiguous thin vessel wall, 3: contiguous multicell thick vessel wall) (n=4 separate sections, n=4 samples).

Statistical Analysis

Data is represented as Mean±S.D. Differences between paired data were compared using Student's t-test, and ANOVA with Tukey post hoc analysis for multiple comparisons of parametric data and Kruskal-Wallis ANOVA with Dunn's post hoc analysis for non-parametric data. Values of $p<0.05$ were considered statistically significant.

Example 1

Physical and Structural Characterization of SLanc

Figure 1I:
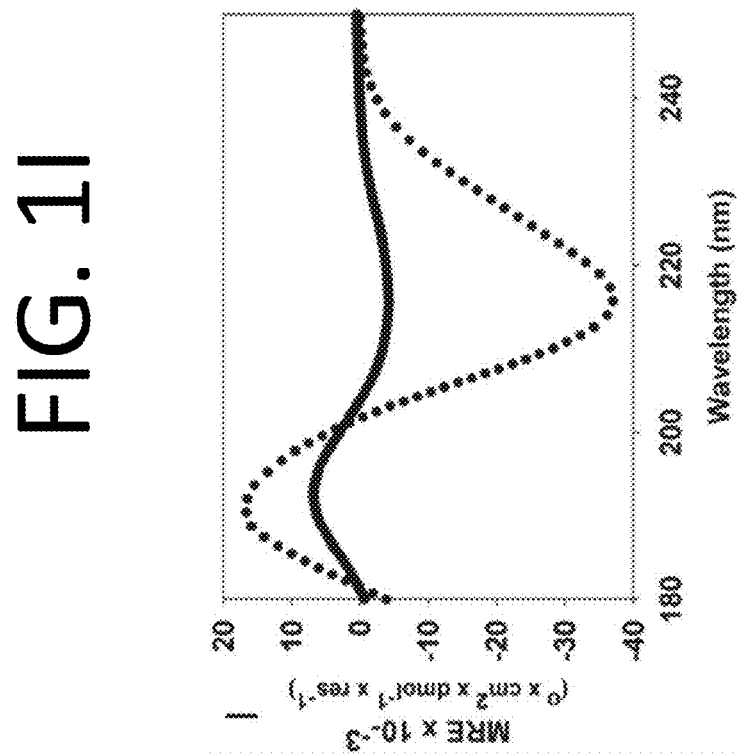
FIG. 1I is a graphical representation of circular dichroism showing presence of beta sheet supramolecular within polymer structure (solid line) of SLanc which is enhanced by the addition of polyvalent salts (dotted line).
Figure 1H:
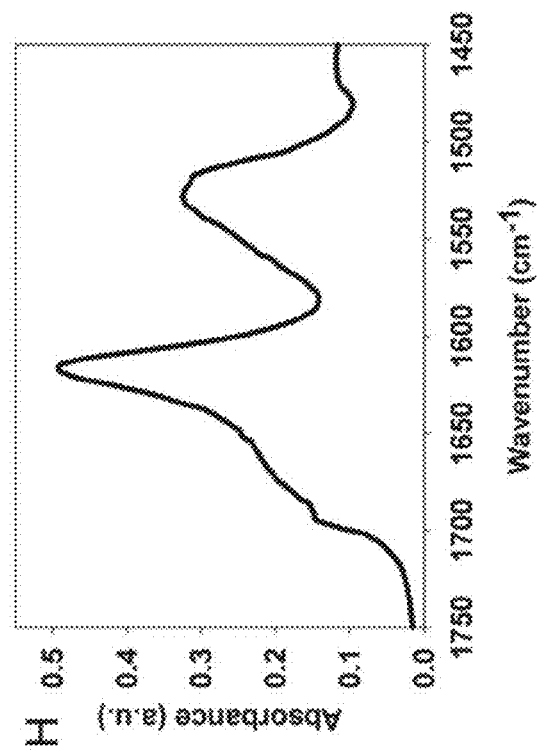
FIG. 1H provides a FTIR spectrum showing characteristic amide I band (1625 cm-1 peak) and anti-parallel (1695 cm-1 peak) beta sheet formation of SLanc.

A schematic of SLanc with its peptide sequence demonstrates the fiber formation (FIG. 1A). Purified and lyophilized SLanc was dissolved in 298 mM sucrose aseptically at 2 w % and stored at room temperature till use. With the addition of multivalent salts such as $PO_4^{3-}$ in buffered solutions at a 1:1 volumetric ratio with SLanc solutions (FIG. 1B) a robust hydrogel forms (FIG. 1C). FITC conjugated SLanc can be used to dope SLanc at a concentration of 1:100 yielding fluorescent gels (FIG. 1D). Mechanical characterization of peptide scaffolds showed responsivity of hydrogels to high frequency shear, with gels breaking (inversion of G' and G") at about 15 rad/s (FIG. 1E). Further gels demonstrate strain shearing at about 20% strain (FIG. 1F). To demonstrate syringe aspiration and delivery, hydrogels were sheared at high strain rates (100% strain) for 1 minute and then returned to low strain (1% strain). Hydrogels recover greater than 95% of their storage moduli within seconds of returning to low strain. This suggests the ability of hydrogels to shear thin and recover rapidly. Furthermore, SLanc self-assembles into β-sheets as shown in the characteristic CD peaks. Further, FTIR of MDP peptides and SLanc reveal folding to occur in anti-parallel β-sheets (FIGS. 1G & H). Ultrastructural analysis of SLanc shows a nanofibrous hydrogel scaffolds under SEM with the presence of fibrils under TEM (FIGS. 1I & J).

Example 2

Chemical Functionality of SLanc

Figure 2A:
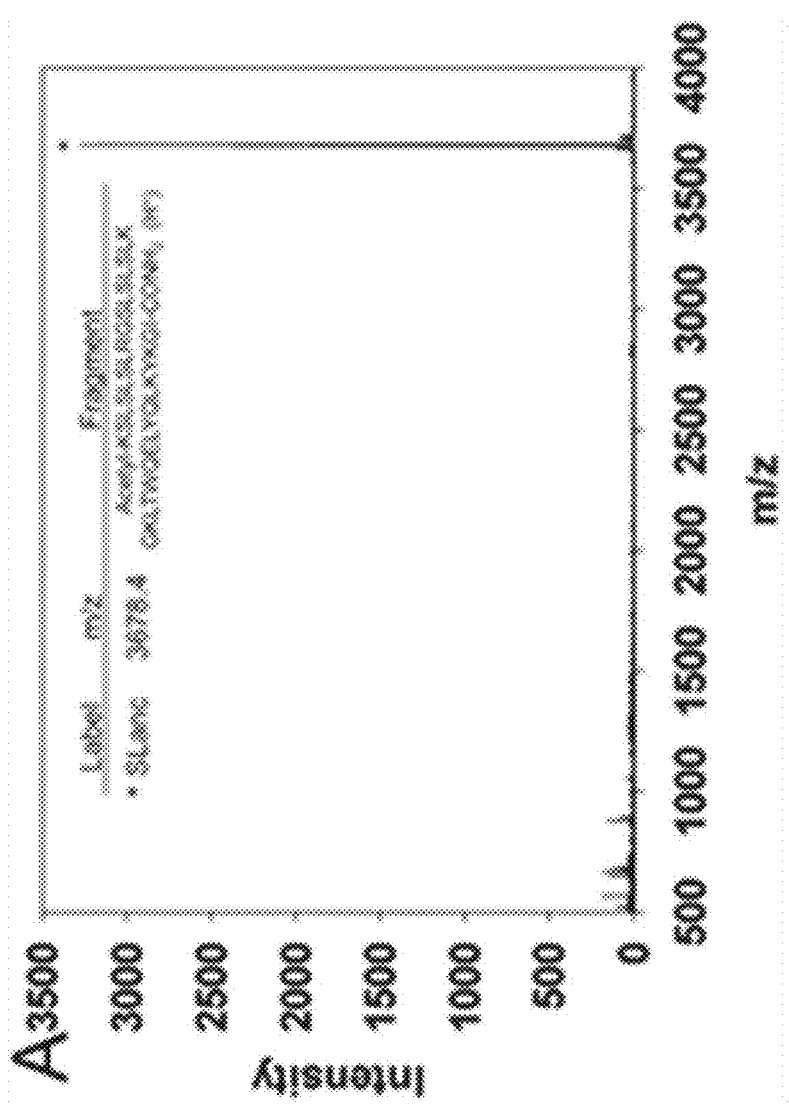
FIG. 2A provides MALDI-mass spectrometry data on intact SLanc before incubation with MMP-2.
Figure 2B:
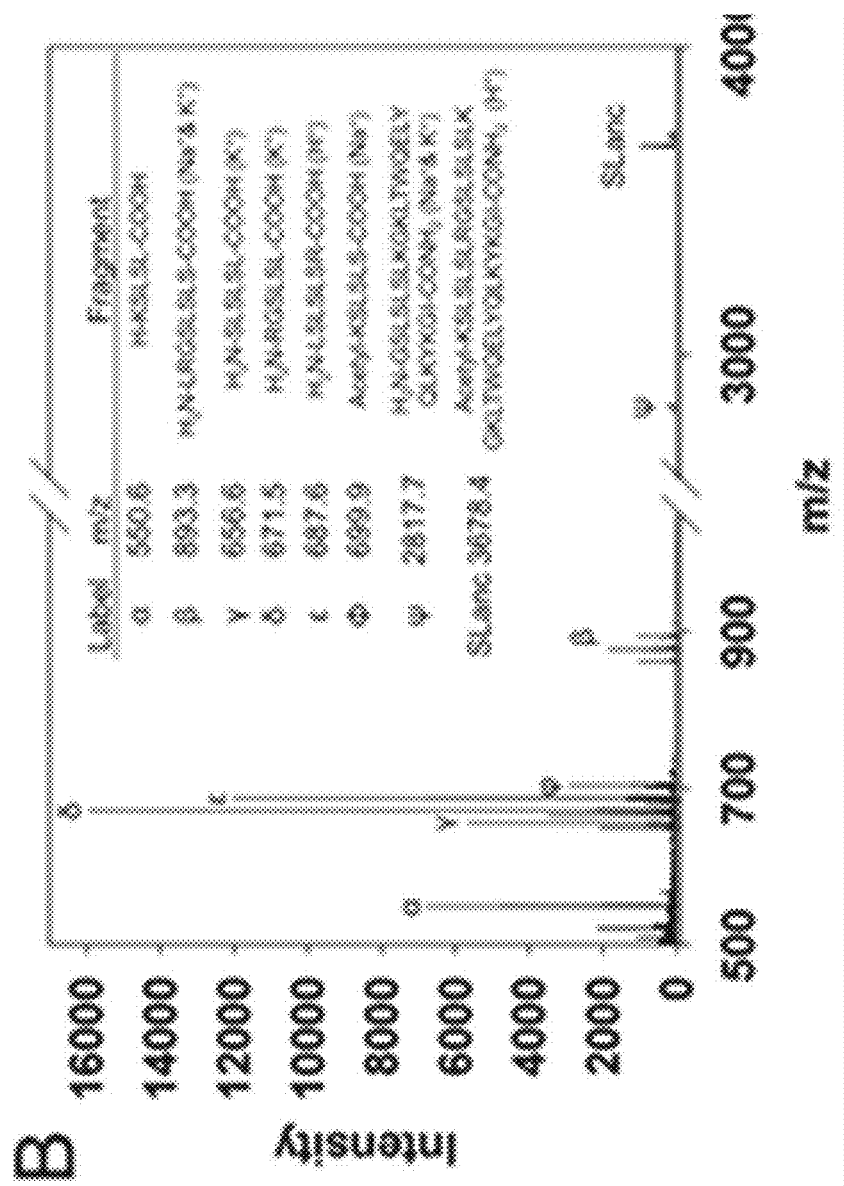
FIG. 2B provides MALDI-mass spectrometry data showing the cleavage fragments of SLanc after incubation with MMP-2.
Figure 2C:
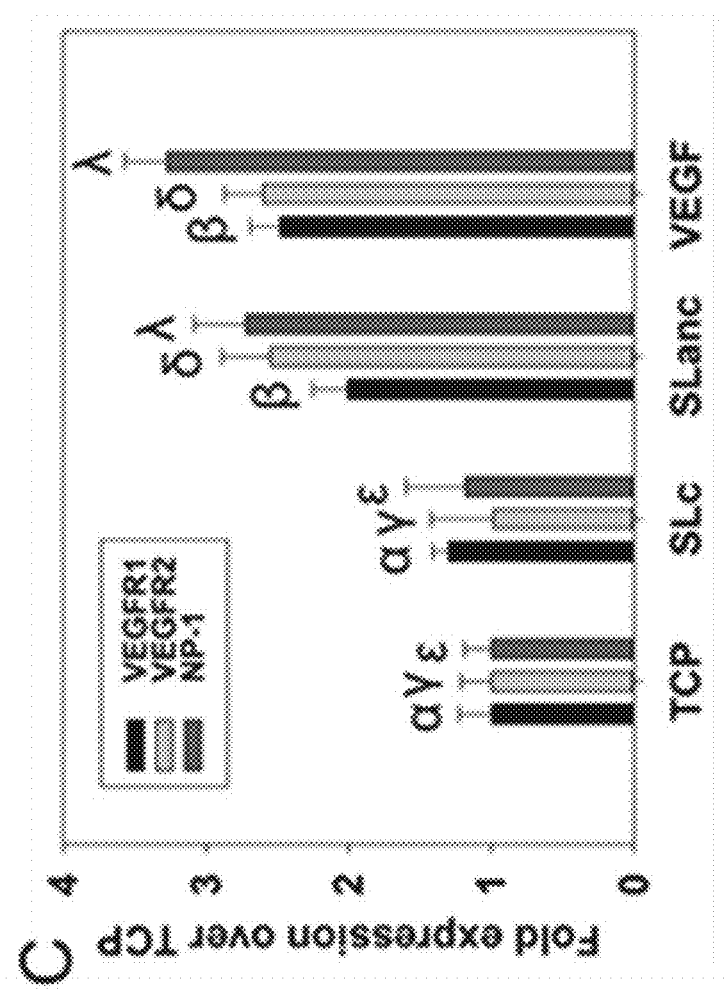
FIG. 2C is a graph representing activation of VEGF receptors shown by PCR of VEGFR-1/2 and NP-1 upon interaction with different peptides compared to SLanc or VEGF positive control. Similar Greek letter indicates no statistically significant difference (*p<0.01).

Chemical moieties introduced into the peptide sequence can tailor the host response to materials. In the design of SLanc, an MMP-2 cleavage sequence was introduced into the central peptide backbone. This sequence can be cleaved specifically with MMP-2, which is secreted by a host of infiltrating cells ranging from macrophages to fibroblasts. In vitro demonstration of physiological degradation of SLanc with the addition of MMP-2, yields a variety of peptide fragments around the cleavage site (FIGS. 2A & B). Additional functionality was afforded to SLanc to enhance angiogenesis by addition of QK derived from VEGF-165. HUVEC vasculogenic receptor activation was determined by PCR indicating that similar levels of VEGFR1, VEGFR2 and NP-1 receptor activation for SLanc and VEGF doped media, compared to TCP or SLc (FIG. 2C). Together chemical, mechanical and structural data demonstrate the development of an injectable self-assembling nanofibrous scaffolds that capable of being degraded and activating vasculogenic receptors.

Example 3

Cytocompatibility of SLanc

Figure 3A:
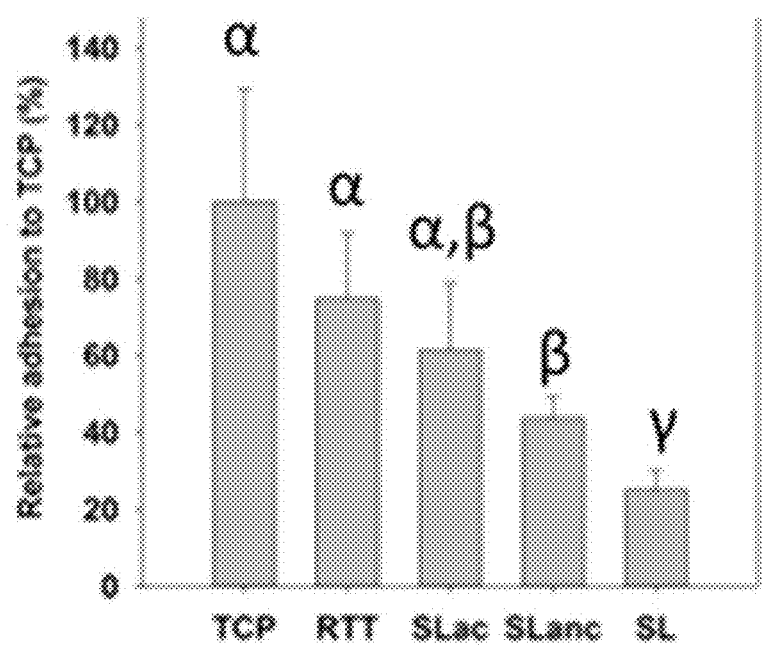
FIG. 3A is a graphical representation quantifying the adhesion of various peptides to hMSCs. As depicted therein, TCP showed greatest adhesion, while RGD modified SLac and angiogenic SLanc showed similar cell adhesion.
Figure 3I:
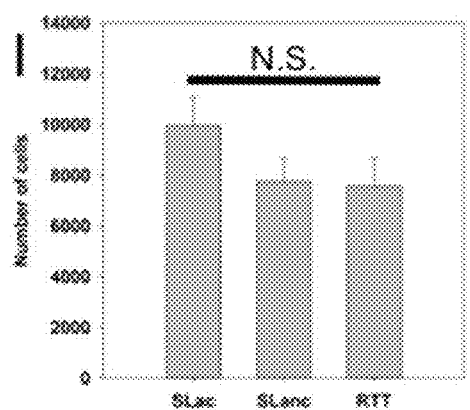
FIG. 3I provides a graph quantifying the HUVEC adhesion on various scaffolds and demonstrates that HUVEC proliferated to a similar extent on all hydrogel material surfaces after 4 days.
Figure 3J:
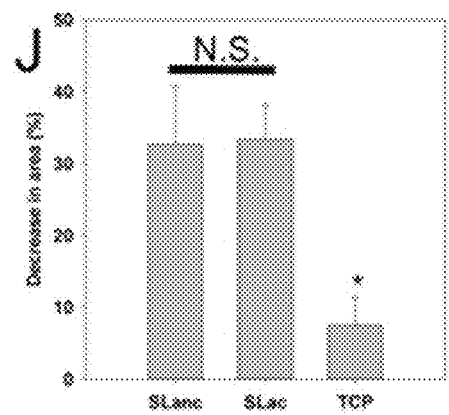
FIG. 3J provides a graphical representation of migration of HUVEC into a scratch wound with various soluble peptide stimuli. Conditions were in low FBS (0.5%) media after 18 hr. SLac and SLanc showed significantly higher proliferation than TCP.

While cytocompatibility is generally thought to be conferred by ECM mimicking structures, peptide primary structure and functionality may drastically effect cell viability and proliferation. To assay cytocompatibility, three different cell types were used. First human mesenchymal stem cells (hMSCs) were seeded onto hydrogel scaffolds, and showed increased adhesion to SLanc over non-functionalized scaffolds. Further, SLanc showed similar cell adhesion to MDP scaffolds modified with fibronectin derived RGD, SLac (FIG. 3 A-F). Scaffolds immunogenicity to activate a pro-inflammatory M1 macrophage phenotype was assayed by incubating THP-1 cells atop scaffolds. TNF-α and IL-1β levels determined by ELISA for SLanc scaffolds were significantly lower than LPS activated cells, with levels similar to commercially available scaffolds (Puramatrix™ and Matrigel™) (FIGS. 3 G & H). Finally, HUVEC cytocompatibility was evaluated to determine ability of endothelial cells to proliferate on scaffolds. Endothelial cells showed proliferation on SLanc scaffolds similar to SLac scaffolds with similar scratch wound healing cellular infiltration (FIG. 3 J-L).

Example 4

In Vivo Angiogenic Response of SLanc

Figure 4A:
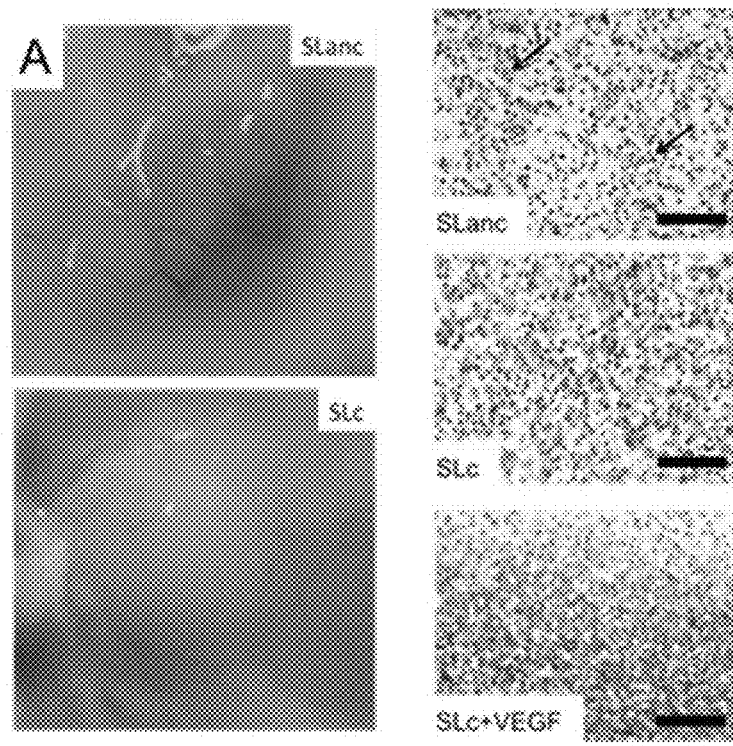
FIG. 4A provides data related to an in vivo evaluation of SLanc compared to SLc and SLc+VEGF where, upon explant, SLanc scaffolds showed visible macro-scale vessels compared to SLc (right panels) or SLc-VEGF scaffolds (left panels). The left panels provide H&E staining which demonstrate rapid infiltration of scaffolds and presence of blood vessels in SLanc scaffolds (arrows), scale bar 100 μm.
Figure 4D:
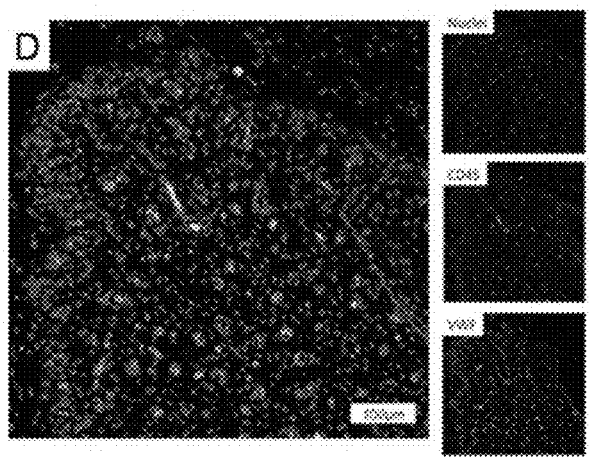
FIG. 4D depicts circulating cells of hematopoietic origin stain positive for CD45 (purple) in endothelial lined (vWF+) vessels.

In modeled diseases such as ligated femoral artery ischemic limb wounds or myocardial infarction several host tissue responses are activated. From secretion of mediators of inflammation such as MCP-1, IL-4, IL-10, SDF-1 and GCSF to growth factors such as VEGF, FGF and EGF extrinsic factors can drastically influence performance of novel materials. As such, prior to use in a disease model, evaluation of scaffolds without concomitant influence from native immune responses was critical. 200 µL subcutaneous implants were randomly made in the dorsal aspect of Wistar rats between the cervical and lumbar vertebrae and 1-2 cm lateral to the midline. 1 w % scaffolds were prepared aseptically by crosslinking 2 w % peptide with an equal volume of HBSS, and injected via 21 gage needle below the skin. At 3 day, 1 week, 2 week and 3 week timepoints, rats were euthanized and scaffolds with surrounding tissue and skin removed. Scaffolds were trimmed, fixed in formalin, embedded in paraffin, sectioned and (immuno-) stained. H&E staining of injected scaffolds showed that SLc and SLc+VEGF showed similar cellular infiltration, with significantly fewer cells and degree of infiltration compared to SLanc scaffolds (FIGS. 4 A, E & F). VEGF-PBS and Puramatrix subcutaneous injections could not be found at the 3 day or subsequent timepoints. These scaffolds seemed to have completely diffused away or degraded 3 days post-implant. SLanc scaffolds showed small nascent vessels at 3 day, but mature Nestin+, α-SMA+, and CD31+ cells at 7 day (FIGS. 4 B and C) and 2 weeks. Further, CD45+ hematopoietic cells were noted within vWF+ vessels suggesting patent perfused mature neovessels, which were quantified (FIGS. 4 D, G & H). Development of blood vessels is dependent on the stimuli the host and scaffold provides. VEGF loaded scaffolds presented 100 ng of recombinant protein (13 nM) within scaffolds. However, since every peptide chain in the self-assembling hydrogel had the VEGF mimetic, SLanc scaffolds had an effective VEGF (mimic) concentration of 2.7 mM. Further, SLc and similar MDP scaffolds show extensive and rapid host cell infiltration. These cells of immune, hematopoetic and mesenchymal origin provide a niche for reconstitution of scaffolds. Coupled with recruitment and growth of endothelial feeders from existing vessels, we posit that pericytic cells enhance stability of growing vessels in a paracrine fashion providing adequate support for generation of arterioles. While these vessels are robust and patent, at the 1 week and 2 week timepoints, implants could not be identified in gross histology at 3 weeks, suggesting they are readily resorbed. The importance of this design strategy is underscored by the rapid development of angiogenic networks (within 3 days), stable vessels (within 7 days), and resorption of vessels and implants without development of hemangiomas or hemorrhaging (within 3 weeks). This novel angiogenic material may prove valuable for the treatment of ischemic tissue disease where multiple biweekly injections can promote and regulate tissue healing.

A variety of VEGF mimics have been used previously. Since its identification and isolation in 2005, this VEGF-165 mimic, QK, has shown to be highly conserved, stable in secondary structure and activate a host of VEGF receptors. Stemming from this, several groups have conjugated QK to surfaces, PEG hydrogels, and other self-assembling peptides. These studies affirm QK stimulates VEGF receptor activation, dimerization, and can potentially stimulate tissue regeneration. However, these studies and others to date have yet to achieve the three required criteria for functional angiogenic vessel development: (1) retention of vessels; (2) stabilization of vessels with pericytes/SMC; and (3) resorption after 2-3 weeks to prevent hemangiomas. In these Examples, we assayed the effects that SLanc (MDP-QK scaffolds) had on self-assembly, cells and in vivo.

The results demonstrate that SLanc scaffolds still formed β-sheet based nanofibrous hydrogels, while stimulating VEGF receptors. Having confirmed cytocompatibility, the results demonstrate rapid infiltration by cells and development of stable perfused vasculature within 7 days, that resorb by 3 weeks. Infiltrating cells result in molecular reorganization of scaffolds, pre-loading scaffolds with necessary vascular support cells, as seen in 3 day histology. Further, a small amount of SLanc disassembles and diffuses towards native vasculature, prompting budding and growth of feeder vessels to the implant. Due to the lack of a fibrous capsule, communication inside and outside scaffolds is possible. Finally, infiltrating vessels mature by support cells leading to perfused microvessels. These infiltrating cells and vessels reorganize the scaffolds, secrete their own matrix and mature over the first 2 weeks. After 2 weeks, we note that vessels resorb into the host tissue, suggesting that the highly perfused scaffolds are infiltrated, digested and biodegraded.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition comprising:
a peptide comprising a first domain, a second domain, a third domain, a fourth domain, and a fifth domain, wherein:
the first domain is $(X)_n$, where X is a negatively or positively charged amino acid, and n is 1 to 4, wherein the first domain is positioned at both the N-terminal and C-terminal ends of the second domain;
the second domain is $(YZ)_{n'}$, where Y is a hydrophilic amino acid and Z is a hydrophobic amino acid or Y is a hydrophobic amino acid and Z is a hydrophilic amino acid, and n' is 2 to 8;
the third domain is an enzymatic cleavage signaling sequence;
the fourth domain is a spacer; and
the fifth domain is a bioactive peptide sequence of SEQ ID NO: 36.

2. The composition of claim 1 wherein X is selected from the group consisting of glutamic acid, aspartic acid, arginine, histidine, lysine.

3. The composition of claim 1 wherein Y is serine and Z is leucine and n' is 6.

4. The composition of claim 1 wherein the hydrophobic amino acid is selected from the group consisting of alanine, leucine, glycine, isoleucine, tryptophan, phenylalanine, proline, methionine, and cysteine, and the hydrophilic amino acid is selected from the group consisting of serine, tyrosine, threonine, asparagine, and glutamine.

5. The composition of claim 1 wherein the enzymatic cleavage signaling sequence is leucine-arginine-glycine.

6. The composition of claim 1 wherein the spacer is selected from the group consisting of aminohexanoic acid, polyethyleneglycol, 5 or fewer glycine residues, and 3 or fewer of SEQ ID No: 95.

7. The composition of claim 1 wherein X is lysine and n is 1, wherein Y is serine and Z is leucine and n' is 6, wherein the enzymatic cleavage signaling sequence is leucine-arginine-glycine, and wherein the enzymatic cleavage signaling sequence is located after the third leucine in the second domain such that the leucine of the enzymatic cleavage sequence is provided by the third leucine of the second domain, wherein the spacer is glycine.

8. The composition of claim 7 wherein the peptide is in a solution at a concentration from about 0.10 mg/ml to about 100 mg/ml, wherein the solution comprises sucrose, and wherein the composition further comprises a buffer having negatively-charged ions, wherein the ratio of the buffer to the solution is 1:1 by volume.

9. The composition of claim 7 wherein the peptide is in a solution at a concentration of about 20 mg/ml, wherein the solution comprises sucrose, and wherein the composition further comprises a buffer with negatively-charged ions, wherein the ratio of the buffer to the solution is 1:1 by volume.

10. The composition of claim 1 further comprising a buffer, wherein the buffer comprises negatively-charged ions when X is a positively-charged amino acid and comprises positively-charged ions when X is a negatively-charged amino acid, and wherein the peptide is at a final concentration from about 0.05 mg/ml to about 50 mg/ml.

11. The composition of claim 10 wherein the final concentration of peptide is greater than 5 mg/ml and less than or equal to 50 mg/ml, wherein the peptide has an initial storage modulus at 1% strain, wherein the initial storage modulus is greater than 90% recoverable within about 90 seconds following exposure to shearing at 100% strain for one minute.

12. The composition of claim 1 wherein the third domain is positioned within the second domain.

13. A method comprising:
    administering a composition as provided in claim 10 or 11 to a target location of a subject; and
    allowing the composition to form a hydrogel scaffold at the target location following administration.

14. The method of claim 13 wherein the step of administering the composition is performed by injection.

15. The method of claim 14 wherein the final concentration of the peptide in the composition is from about greater than 5 mg/ml to about 50 mg/ml.

16. The method of claim 14 wherein the final concentration of the peptide in the composition is about 20 mg/ml.

17. The method of claim 14 wherein the final concentration of the peptide in the composition is about 10 mg/ml.

18. The method of claim 13 wherein the subject is a human patient suffering from an ischemic wound, and wherein the target location is the ischemic wound.

* * * * *

SEQUENCE LISTING

```
<160> NUMBER OF SEQ ID NOS: 95

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ser Leu Ser Leu Ser Leu Arg Gly Ser Leu Ser Leu Ser Leu Lys
1               5                   10                  15

<210> SEQ ID NO 2
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Tyr Pro Val His Pro Ser Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Pro Leu Gly Asn Ser His
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu His Tyr Pro Phe Met Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Pro Leu Gly Asn Ser His
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Thr Thr Ser Pro Thr Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Val Pro Pro Ala Asn Thr
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Thr Gln Ala Gln His
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Arg Asn Tyr Ser His Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Lys Tyr Pro Pro Thr Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Gln Ala Leu Thr Gln Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Ile Gln Pro Asp Glu Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Val Tyr Arg His Leu Pro Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Trp Lys Ser Val Thr Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Pro Ala Leu Phe Thr His
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Phe Asp Pro Pro Val Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Val Ser Thr Trp Asp Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Ser Pro Ile Gln Lys
1               5

<210> SEQ ID NO 19
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 19

Pro Gly Pro Thr Val Gln Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Val Ser Pro Ala Tyr His
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Ala Pro Arg Trp Ile His
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Pro Val His Pro Ser Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Pro Leu Gly Asn Ser His
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Pro Thr Trp Val Asn Asn
1               5
```

```
<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Thr Pro Leu Lys Val Arg Leu His Ser Tyr Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Tyr Thr Val His His Met
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp His Trp Ser Leu Asn His
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Ser Ile Leu Ser Thr Ile Pro Asn Ser Met Thr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Trp Trp Ala Pro Phe His
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Phe Thr Glu Pro Leu Ala Ser
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Leu Thr Pro Ser Ala Leu Leu Pro Ile Phe Glu
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr His Ala Phe Arg Val Met
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ser Leu Phe Ser Ser Asn
1               5

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Pro Gln Lys Asn Thr Ile Gln Tyr Glu Lys Met Leu Leu Thr Val
1               5                   10                  15

Ser Ser Tyr

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Pro Tyr Pro His Tyr His
1               5
```

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Leu Thr Trp Gln Glu Leu Tyr Gln Leu Lys Tyr Lys Gly Ile
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Met His His His Lys His
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Gln Val Arg Ser Gly Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys His Pro Pro Thr Asn Trp
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Met Leu Ser His Leu Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

-continued

```
Asp Phe Ile Gln Pro Tyr Gln
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Tyr Trp Ser Arg Ile Glu
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Met Pro Gln Arg Pro Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Ser Arg His Phe His His
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Met Thr Gln Val Pro Leu
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ser Thr Pro Pro Leu Arg
1               5

<210> SEQ ID NO 47
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

His Thr Thr Glu Ile Leu His
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Ser Asn Tyr Gln Thr Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Tyr Phe Pro Ser Ser Ala
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Ala Arg Gln Ser Tyr Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Glu Pro Gln Lys Ala His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Leu Gly Leu Gly Leu His
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Met Arg Arg Ser Leu Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Val Leu Tyr Leu Pro Leu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Lys Leu Asn Thr Lys Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Thr Tyr His His Arg His
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Arg His Lys Ser Leu His
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Arg Tyr His Pro His Leu His
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Arg Tyr His His Tyr Leu His
1               5

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Ile Pro Lys Ala Ser Ser Val Pro Thr Glu Leu
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Arg Thr Gly Gln Tyr Lys Leu
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Arg Gly Asp Ser Pro
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Arg Gly Glu Ser Pro
1               5

<210> SEQ ID NO 64
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 64

Ser Val Val Tyr Gly Leu Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Lys Lys Thr Glu Thr Gln
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Gly Val Ala Pro Gly
1               5

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Glu Asp Val
1

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Arg Gly Asp Ser Gly Tyr Arg Gly Asp Ser
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Lys Leu Thr Trp Gln Glu Leu Tyr Gln Leu Lys Tyr Lys
1               5                   10                  15

Gly Ile

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Asp Pro Gly Tyr Ile Gly Ser Arg
1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Arg Asn Ile Ala Glu Ile Ile Lys Asp Ile
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Ile Thr Tyr Val Arg Leu Lys Phe
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ile Thr Val Thr Leu Asn Arg Leu
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Arg Tyr Val Val Leu Pro Arg
1               5

<210> SEQ ID NO 75
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 75

Gly Asn Arg Trp His Ser Ile Tyr Ile Thr Arg Phe Gly
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Ile Asp Gln Val Glu Pro Tyr Ser Ser Thr Ala Gln
1               5                   10

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ile Pro Lys Ala Ser Ser Val Pro Thr Glu Leu Ser Ala Ile Ser
1               5                   10                  15

Thr Leu Tyr Leu
            20

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Lys Gln Arg Phe Arg His Arg Asn Arg Lys Gly
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ala Ser Ile Lys Val Ala Val Ser Ala Asp Arg
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Thr Thr Val Lys Tyr Ile Phe Arg
```

```
<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Ile Lys Ile Arg Gly Thr Tyr Ser
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Ile Asn Asn Asn Arg
1               5

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Lys Ser Leu Ser Leu Ser Leu Arg Gly Ser Leu Ser Leu Ser Leu Lys
1               5                   10                  15

Gly Lys Leu Thr Trp Gln Glu Leu Tyr Gln Leu Lys Tyr Lys Gly Ile
            20                  25                  30

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Lys Ser Leu Ser Leu Ser Leu Ser Leu Ser Leu Ser Leu Lys Lys
1               5                   10                  15

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Lys Ser Leu Ser Leu Ser Leu Arg Gly Ser Leu Ser Leu Ser Leu
1               5                   10                  15

Lys Lys

<210> SEQ ID NO 86
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ser Leu Ser Leu Ser Leu Arg Gly Ser Leu Ser Leu Ser Leu Lys
1               5                   10                  15

Gly Arg Gly Asp Ser
            20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tcccttatga tgccagcaag t                                              21

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccaaaagccc ctcttccaa                                                 19

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
caccactcaa acgctgacat gta                                            23

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gctcgttggc gcactctt                                                  18

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atcacgtgca gctcaagtgg                                                20
```

```
<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tcatgcagtg ggcagagttc                                                     20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
attgaaatca gccagcacgc                                                     20

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aggaaccaca gtgccagatc c                                                   21

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Ser Gly
1
```